US00PP20190P2

(12) United States Plant Patent
Orozco

(10) Patent No.: US PP20,190 P2
(45) Date of Patent: Jul. 28, 2009

(54) APPLE TREE NAMED 'FUGACHEE'

(50) Latin Name: *Malus domestica Borkh*
Varietal Denomination: Fugache

(75) Inventor: Gaspar S. Orozco, Bridgeport, WA (US)

(73) Assignee: Fugachee Orchards Partnership, Brewster, WA (US)

( * ) Notice: Subject to any disclaimer, the term of this patent is extended or adjusted under 35 U.S.C. 154(b) by 0 days.

(21) Appl. No.: 12/072,617

(22) Filed: Feb. 26, 2008

(51) Int. Cl.
*A01H 5/00* (2006.01)

(52) U.S. Cl. ..... Plt./172
(58) Field of Classification Search ..... Plt./172, Plt./161
See application file for complete search history.

*Primary Examiner*—June Hwu
(74) *Attorney, Agent, or Firm*—Klarquist Sparkman, LLP

(57) ABSTRACT

The Fugachee apple is a new and distinct cultivar, yellow green in skin color with prominent russetted lenticels, conical shape, smooth apical basin (non-lobed), with a distinctive, low-acid, sweet flavor and excellent, crisp, juicy, texture.

4 Drawing Sheets

Latin name of the genus and species of the plant claimed: *Malus domestica Borkh.*
Variety denomination: 'Fugachee'.

BACKGROUND OF THE INVENTION

The new cultivar, denominated 'Fugachee', is a new and distinct cultivar of apple, *Malus domestica,* 'Borkh', which was discovered in 2001 in Bridgeport, Wash. The original apple tree of my new variety was growing in a cultivated block of 'Golden Delicious' (non-patented) apple trees. The original tree is a seedling tree of unknown parentage. In September of 2001, the inventor noticed a single tree with fruit distinctly different from that of the other trees in the block. The inventor continued to observe this tree in 2002 and confirmed that it was a unique variety. In 2003, in Brewster, Wash. 20 to 25 buds from the original tree were budded onto Malling 26 (M26) (unpatented) rootstocks to asexually propagate this new cultivar. These trees first produced fruit in 2005 and were all identical to the original tree.

BRIEF SUMMARY OF THE INVENTION

The following unique combination of characteristics are outstanding in the new variety and distinguish the new variety from all varieties known to the inventor:

1. Uniform, yellowish-green skin color distinctly different from that of 'Golden Delicious' (unpatented), 'Granny Smith' (unpatented), or any other late-maturing variety.
2. Prominent widespread brownish lenticels over the entire fruit surface.
3. Sweet, low-acid flavor, yet crisp, juicy texture.
4. Excellent storage capacity. Comparable to that of 'Granny Smith' or 'Red Delicious' (unpatented) and superior to that of 'Golden Delicious'.

Asexual reproduction of this new variety by cuttings (both hardwood and softwood), as performed at Wasco and Somis, Calif. shows that the foregoing and all other characteristics and distinctions come true to form and are established and transmitted through succeeding propagations.

Figure 1:
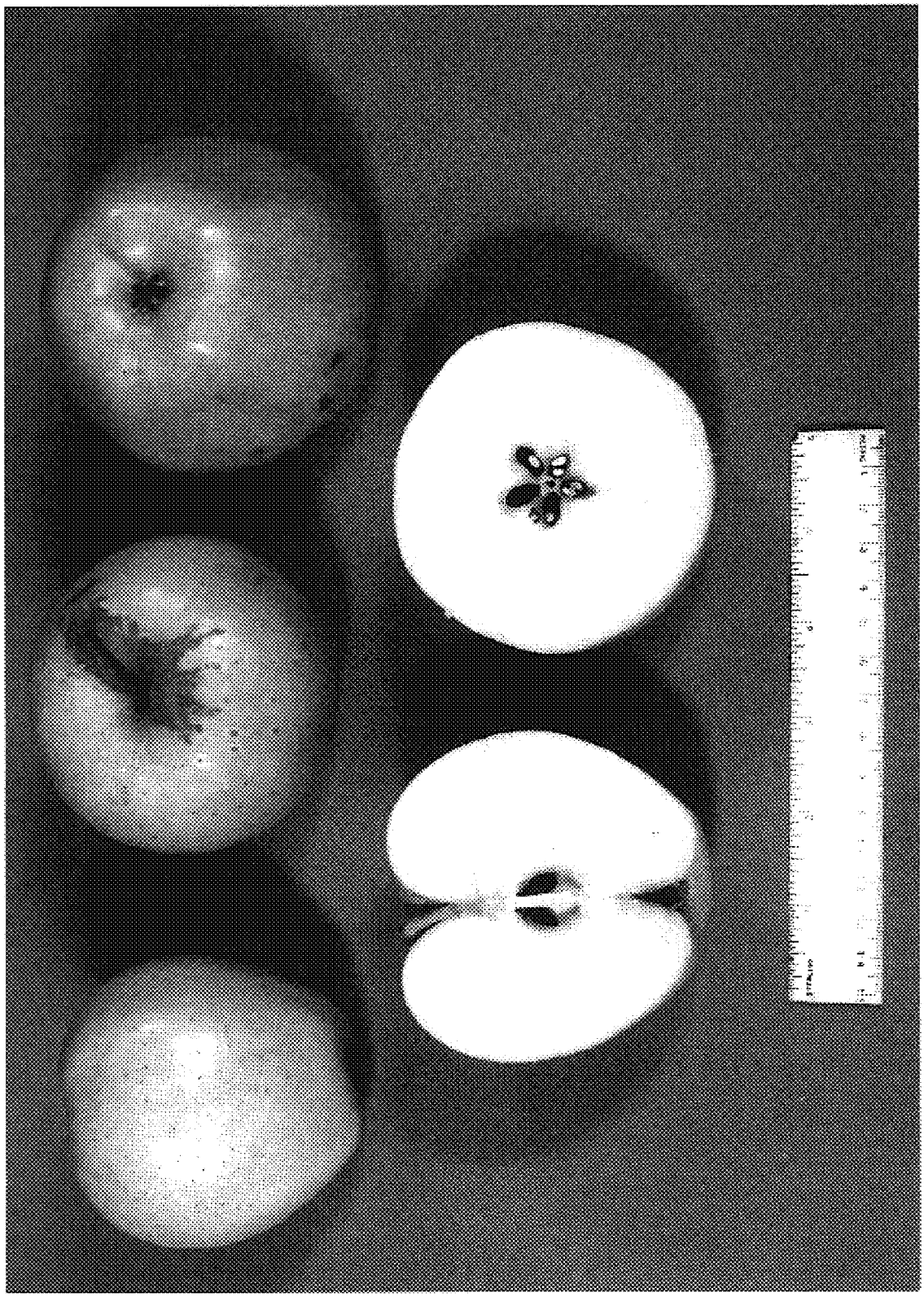
FIG. 1 shows various aspects of 'Fugachee' fruit showing cavity, basin, and transverse and longitudinal sections.
Figure 2:
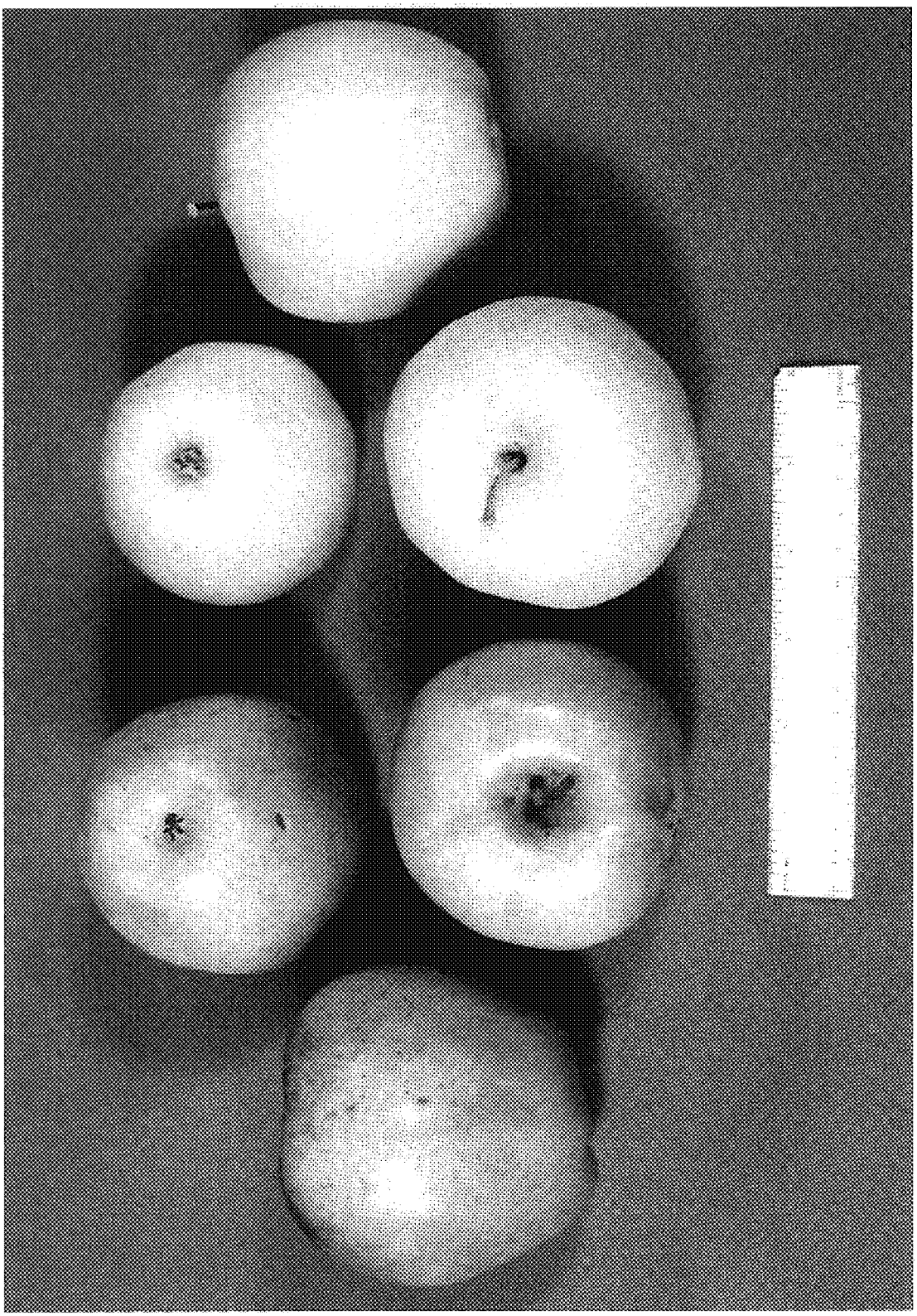
FIG. 2 shows a comparison of 'Fugachee' fruit (to the left in FIG. 2) with Golden Delicious fruit (to the right in FIG. 2).
Figure 3:
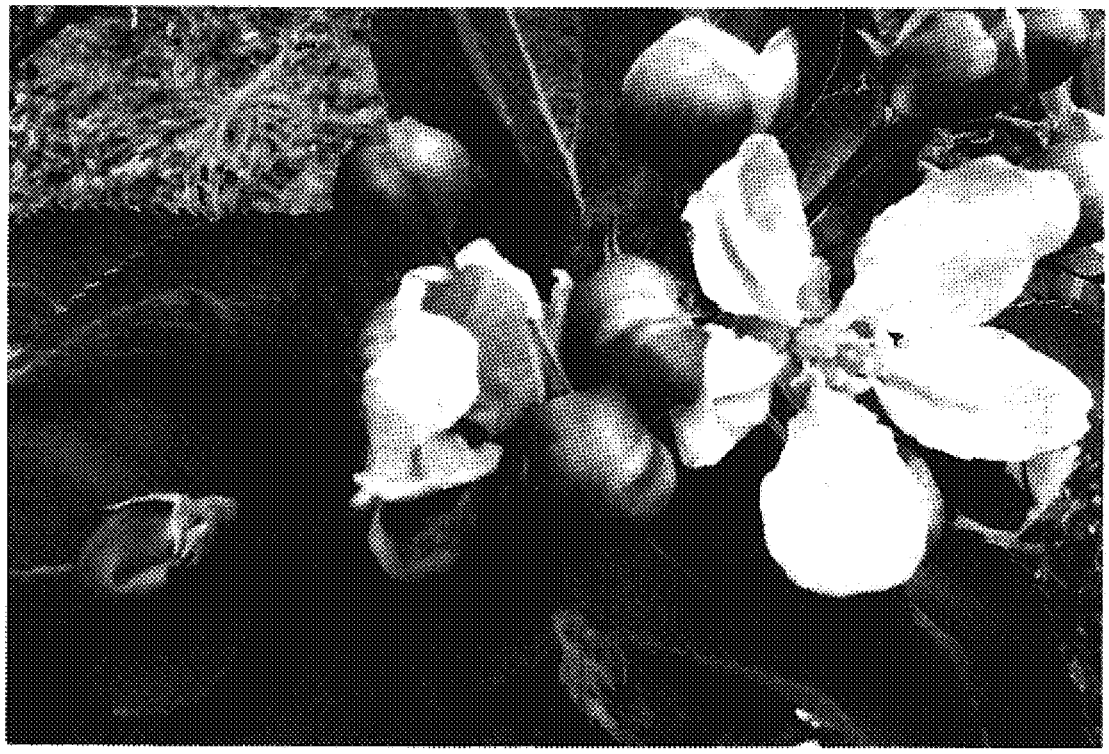
FIG. 3 shows blooms of 'Fugachee' at early bloom (May 1, 2007)
Figure 4:
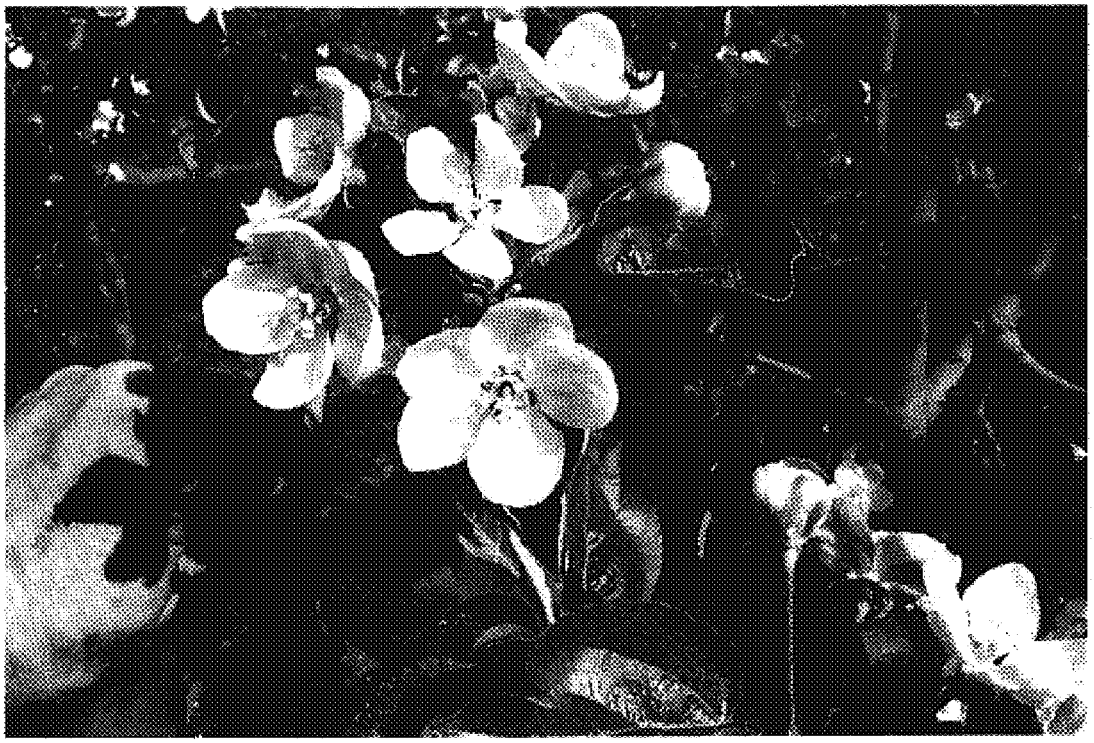
FIG. 4 shows blooms of 'Fugachee' at full bloom stage (May 10, 2007).

Certain characteristics of this variety, such as growth and color, may change with changing environmental conditions, e.g., photoperiod, temperature, moisture, soil conditions, nutrient availability, or other factors. Color descriptions and other terminology are used in accordance with their ordinary dictionary descriptions, unless the context clearly indicates otherwise. Color designations (hue/value/chroma) are made with reference to the Munsell Book of Color, Kollmorgen Instruments Corp., 405 Little Britain Road, New Windsor, N.Y. 12553.

The following detailed description of the 'Fugachee' cultivar apple tree is based on observations of the approximately four-year-old second-generation trees budded from the original tree and growing in Bridgeport, Wash.

Scientific name: *Malus domestica* Borkh.
Varietal name: 'Fugachee'.
Parentage: Original tree grew as a seedling tree of unknown parentage.
Tree: Second generation trees budded from original tree in 2003.
- *Height.*—3m (about 9 feet).
- *Width.*—2m (about 6 feet).
- *Overall shape.*—Upright spreading, similar to 'Golden Delicious'.
- *Vigor.*—High; average seasonal growth in Brewster approximately 60 to 90 cm.
- *Productivity.*—Annually productive when properly thinned.
- *Chilling requirement.*—Unknown.

Trunk:

*Size.*—10 cm in diameter at 0.5 m from graft union.

*Trunk bark texture.*—Smooth with raised lenticels, about 4 per square cm, similar to that of 'Golden Delicious'.

*Trunk bark color.*—Tan (7.5 YR 4/4).

Branches:

*Habit.*—Upright to spreading, similar to 'Golden Delicious'. Branch angles are typically 50 to 65 degrees from the vertical.

*Size and texture.*—Similar to that of 'Golden Delicious'.

*Branch color.*—One-year-shoot bark color ranges from green (2.5 GY 5/4) to brown (7.5 YR 4/4).

*Branch pubescence.*—Glabrous to very fine colorless pubescence at nodes.

*Branch lenticels.*—Square, inconspicuous. Very small (0.5×0.5 mm); light tan (7.5 YR 6/2).

*Internodes.*—Average internode length on one-year shoots 3.5 cm.

Leaves: (Based on observations of ten leaves May 10, 2007).

*Texture.*—Smooth, slightly rugose on upper surface.

*Sheen.*—Glossy. Similar to that of 'Golden Delicious'.

*Size.*—Medium to large, length is 10 to 13 cm (average 12 cm) including petiole. Width is 5.5 to 7.5 cm (average 6.3cm). Somewhat larger than 'Golden Delicious'.

*Petiole.*—About 28 to 40 mm in length (average 38 mm). Thickness is 1.5 to 2.5 mm. Mid-petiole color grey green (10 GY 7/2).

*Veins.*—Light green (2.5 GY 8/4).

*Form.*—Oval, tapering to tip.

*Marginal form.*—Crenate to coarsely serrate.

*Tip.*—Ovate to acuminate.

*Stipules.*—1 to 2 per node. Length 6 to 15 mm. 1 to 2 mm in width, lacking on older nodes.

*Leaf color.*—Upwardly disposed surface: dark green (7.5 GY 3/6);

*Downwardly disposed surface.*—Medium green (5 GY 6/6).

*Pubescence.*—Upper surface is sparse to lacking pubescence. Lower surface is moderately pubescent, decreasing with leaf age; almost colorless.

Flowers (Observations from a sampling of second-generation trees in late April, early May, 2007): Buds are round to oval, 10 mm in length, 5 mm in diameter; first bloom was May 1, 2007; full bloom was May 6, 2007; bloom duration was approximately 10 days.

*Size.*—Medium to large, 25 to 40 mm, while 'Golden Delicious' is 35 to 40 mm.

*Bloom description.*—Flowers generally in clusters of 3 to 5 per spur.

*Flower color.*—Pink in bud stage becoming white when fully open. Popcorn buds color pink (5RP 6/10).

*Petals.*—Five in number. Rounded at apex, acute at base compared to 'Golden Delicious' whose obtuse base gives a more rounded appearance of the individual petals. Position of petal margins is separate, whereas in 'Golden Delicious' they are overlapping.

*Stamen.*—Single row, 15 to 20 in number.

*Filament.*—Approximately 10 mm in length, similar to that of 'Golden Delicious'.

*Anthers.*—Unopened are bright yellow (5 Y 8.5/10).

*Pistil.*—Style medium to long, branched into 5 long stigmatic elements (longer than those of 'Golden Delicious').

*Sepals.*—5 in number, 10 mm in length, 3 mm in width (similar to 'Golden Delicious'). Recurved downward, pale green with a slightly reddish tint at the tips (10 Y 8/4), pubescent.

*Peduncle.*—Approximately 18 mm in length (range of 10 to 30 mm). Approximately 2 mm in diameter. Distinctly thicker than in 'Golden Delicious', green to purple in color on exposed side (10 Y 6/6) to (5 R 4/6).

*Fragrance.*—Medium, stronger than that of 'Golden Delicious'.

*Pollination requirements.*—Presumed to be diploid and self-sterile.

Fruit: Maturity when described was early harvest period, Sep. 26, 2007 at Bridgeport, Wash. Maturity of 'Fugachee' is approximately 7 days later than that of 'Golden Delicious'. Firmness was 19 pounds (Taylor-Magness pressure tester); soluble solids was 16%; malic acid content (titration) was 0.4%; starch index (1 to 6 scale) was 3.0.

*Size.*—Very large, about 7.5 to 9 cm. Average weight was 330 grams. Average cross-sectioned diameter was 8.0 cm. Average axial diameter was 8.5 cm.

*Form.*—Oblong conic. Length/diameter ratio approximately 1.06, uniform, no ribbing, distal end slightly lobed.

*Stem cavity.*—Medium width (35–40 mm); medium depth (18 mm); acute, commonly with flaring russet.

*Stem.*—Short to medium length (12 to 27 mm); width 2 mm; color brown (2.5 R 5/4) to greenish (10 Y 6/6), Skin medium thick and tough.

*Lenticels.*—Light tan (2.5 Y 8/2), very prominent, slightly raised. Density 2 to 3 per square cm, about 1 mm in diameter.

*General color effect.*—Yellowish green (midway between 'Granny Smith' and 'Golden Delicious').

*Ground color.*—Green (5 GY 6/8).

*Overcolor.*—Yellow green (2.5 GY 8/10).

*Russet.*—Occasional russet around stem, none on basin.

*Flesh.*—Cream color (10 Y 9/4); juicy, crisp, sweet, similar to that of 'Mutsu' (non-patented); no tendency to become mealy.

*Aroma.*—Typical apple aroma.

*Core.*—Round, medium to large (25 mm width and 38 mm length), 10 bundles, core lines sharply defined, locules mostly open, calyx tube long (15 mm), closed.

*Seeds.*—Obovate in shape, usually 2 per cell; brown (10 YR 3/6), length about 10 to 11 mm, width about 5 mm, with loose adherence to carpel wall.

*Keeping quality.*—Excellent, better than that of 'Golden Delicious', similar to 'Granny Smith'. Remains firm and crisp at room temperature for 2 to 3 weeks.

*Storage.*—Excellent. At least 6 months in common refrigerated storage (32 degrees F.), 10 to 12 months in controlled atmosphere (CA) storage.

*Usage.*—Primarily fresh (dessert). Similar to that of 'Fuji'.

*Disease resistance.*—Similar to that of 'Golden Delicious' but less susceptible to apple scab. Susceptible to bitter pit, as are 'Mutsu' or 'Golden Delicious' on young, high-vigor trees with very fine colorless pubescence.

*Basin cavity.*—Medium width (25 mm); medium depth (15 mm), obtuse.

*Locules* (*carpels*).—Medium to large in size, 5 in number, open.

*Skin.*—Texture is smooth, dull, and not greasy. Prone to russet around stem.

*Stem.*—Short to medium length (12 to 27 mm); width 2 mm; color brown (2.5 R 5/4) to greenish (10 Y 6/6), Skin medium thick and tough.

*Lenticels.*—Light tan (2.5 Y 8/2), very prominent, slightly raised. Density 2 to 3 per square cm, about 1 mm in diameter.

*General color effect.*—Yellowish green (midway between 'Granny Smith' and 'Golden Delicious').

*Ground color.*—Green (5 GY 6/8).

*Overcolor.*—Yellow green (2.5 GY 8/10).

*Russet.*—Occasional russet around stem, none on basin.

*Flesh.*—Cream color (10 Y 9/4); juicy, crisp, sweet, similar to that of 'Mutsu' (non-patented); no tendency to become mealy.

*Aroma.*—Typical apple aroma.

*Core.*—Round, medium to large (25 mm width and 38 mm length), 10 bundles, core lines sharply defined, locules mostly open, calyx tube long (15 mm), closed.

*Seeds.*—Obovate in shape, usually 2 per cell; brown (10 YR 3/6), length about 10 to 11 mm, width about 5 mm, with loose adherence to carpel wall.

*Keeping quality.*—Excellent, better than that of 'Golden Delicious', similar to 'Granny Smith'. Remains firm and crisp at room temperature for 2 to 3 weeks.

*Storage.*—Excellent. At least 6 months in common refrigerated storage (32 degrees F.), 10 to 12 months in controlled atmosphere (CA) storage.

*Usage.*—Primarily fresh (dessert). Similar to that of 'Fuji'.

*Disease resistance.*—Similar to that of 'Golden Delicious' but less susceptible to apple scab. Susceptible to bitter pit, as are 'Mutsu' or 'Golden Delicious' on young, high-vigor trees with very fine colorless pubescence.

*Basin cavity.*—Medium width (25 mm); medium depth (15 mm), obtuse.

*Locules* (*carpels*).—Medium to large in size, 5 in number, open.

*Skin.*—Texture is smooth, dull, and not greasy. Prone to russet around stem.

TABLE 1

Comparison of characteristics of similar late maturity yellow-green apples.*

| | 'Golden Delicious' | 'Fugachee' | 'Orin' | 'Mutsu' |
|---|---|---|---|---|
| One Year Shoot Color | Brown | Greenish-brown | Green | Brown upper Green lower |
| Fruit Blush (%) | 0-20 | 0-5 | 0 | 0-15 |
| Fruit Shape L/D Ratio | 1.08 | 1.00 | 0.97 | 1.03 |
| Fruit Lenticels | Round, small | Elongated | Elongated Conspicuous | Small, round, more sparse than 'Orin' |
| Skin Color | Greenish-yellow | Green with slightly cloudy transparent scarf skin | Uniformly green, no scarf skin | Greenish, no scarf skin |
| Brix (%) | 15.00 | 15.30 | 13.20 | 12.50 |
| Firmness (lbs) | 16.20 | 16.00 | 17.90 | 19.70 |
| Starch | 3.50 | 2.50 | 3.50 | 2.00 |

*Samples of 'Fugachee' were taken from an orchard in Bridgeport, Washington. Samples of 'Golden Delicius', 'Orin', and 'Mutsu' were obtained from an orchard in Wenatchee, Washington. Bridgeport and Wenatchee have similar climates. All of these apples were picked on the same day. 'Orin' and 'Mutsu' are not patented in the U.S.

I claim:

1. A new and distinct variety of apple tree named 'Fugachee' characterized by the combination of yellow green in skin color with prominent russetted lenticels, conical shape, smooth apical basin (non-lobed), with a distinctive, low-acid, sweet flavor and excellent, crisp, juicy, texture.

* * * * *

UNITED STATES PATENT AND TRADEMARK OFFICE

CERTIFICATE OF CORRECTION

PATENT NO. : PP 20,190 P2
APPLICATION NO. : 12/072617
DATED : July 28, 2009
INVENTOR(S) : Gaspar S. Orozco It is certified that error appears in the above-identified patent and that said Letters Patent is hereby corrected as shown below:

Title Page, Item (50) Latin Name: "Fugache" should read -- Fugachee --

Signed and Sealed this

Seventeenth Day of August, 2010

David J. Kappos

David J. Kappos
*Director of the United States Patent and Trademark Office*